United States Patent
Bai et al.

(10) Patent No.: US 10,420,610 B2
(45) Date of Patent: Sep. 24, 2019

(54) SYSTEM AND METHOD FOR VASCULAR TREE GENERATION USING PATIENT-SPECIFIC STRUCTURAL AND FUNCTIONAL DATA, AND JOINT PRIOR INFORMATION

(71) Applicant: HeartFlow, Inc., Redwood City, CA (US)

(72) Inventors: Ying Bai, Belmont, CA (US); Michiel Schaap, Mountain View, CA (US); Charles A. Taylor, Menlo Park, CA (US); Leo Grady, Millbrae, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 15/094,626

(22) Filed: Apr. 8, 2016

(65) Prior Publication Data

US 2016/0296286 A1 Oct. 13, 2016

Related U.S. Application Data

(60) Provisional application No. 62/145,714, filed on Apr. 10, 2015.

(51) Int. Cl.
| | | |
|---|---|---|
| *A61B 34/10* | (2016.01) | |
| *A61B 6/00* | (2006.01) | |
| *G06T 7/00* | (2017.01) | |
| *G16H 50/50* | (2018.01) | |
| *A61B 34/00* | (2016.01) | |
| *G06T 7/11* | (2017.01) | |
| *G06T 7/187* | (2017.01) | |
| *A61B 6/03* | (2006.01) | |

(52) U.S. Cl.
CPC .............. *A61B 34/10* (2016.02); *A61B 6/503* (2013.01); *A61B 6/504* (2013.01); *A61B 6/507* (2013.01); *A61B 34/00* (2016.02); *G06T 7/0014* (2013.01); *G06T 7/11* (2017.01); *G06T 7/187* (2017.01); *G16H 50/50* (2018.01); *A61B 6/032* (2013.01); *A61B 2034/105* (2016.02); *G06T 2207/10072* (2013.01); *G06T 2207/10081* (2013.01); *G06T 2207/10088* (2013.01); *G06T 2207/10104* (2013.01); *G06T 2207/10108* (2013.01); *G06T 2207/30101* (2013.01); *G06T 2207/30104* (2013.01)

(58) Field of Classification Search
None
See application file for complete search history.

(56) References Cited

U.S. PATENT DOCUMENTS

| 8,315,812 B2 | 2/2012 | Taylor |
| 2013/0246034 A1 | 9/2013 | Sharma |

FOREIGN PATENT DOCUMENTS

| EP | 2835750 | 2/2015 |

OTHER PUBLICATIONS

Tamaddon et al. (International Journal of Medical, Health, Biomedical, Bioengineering, and Pharmaceutical Engineering (2014) vol. 8, pp. 325-333).*
Schneider, M. et al., "Tissue metabolism driven arterial tree generation", Med Image Anal., Oct. 2012; vol. 16(7), pp. 1397-1414.
Hamarneh, G. et al., "VascuSynth: Simulating Vascular Trees for Generating Volumetric Image Data with Ground-Truth Segmentation and Tree Analysis", Comput Med Imaging Graph., Dec. 2010, vol. 34(8), pp. 605-616.
Cuenod, C.A., et al.; "Perfusion and vascular permeability: Basic concepts and measurement in DCE-CT and DEC-MRI" Diagnostic and Interventional Imaging, vol. 94, No. 12, Dec. 1, 2013; pp. 1187-1204.
Karch, Rudolf, et al. "A three-dimensional model for arterial tree representation, generated by constrained constructive optimization", Computers in Biology and Medicine, vol. 29, No. 1, Jan. 1, 1999, pp. 19-38.
International Search Report issued in related PCT/US2016/026766, dated Jul. 5, 2016 (14 pgs).

* cited by examiner

*Primary Examiner* — Lori A. Clow
(74) *Attorney, Agent, or Firm* — Bookoff McAndrews, PLLC

(57) ABSTRACT

Systems and methods are disclosed for simulating microvascular networks from a vascular tree model to simulate tissue perfusion under various physiological conditions to guide diagnosis or treatment for cardiovascular disease. One method includes: receiving a patient-specific vascular model of a patient's anatomy, including a vascular network; receiving a patient-specific target tissue model in which a blood supply may be estimated; receiving joint prior information associated with the vascular model and the target tissue model; receiving data related to one or more perfusion characteristics of the target tissue; determining one or more associations between the vascular network of the patient-specific vascular model and one or more perfusion characteristics of the target tissue using the joint prior information; and outputting a vascular tree model that extends to perfusion regions in the target tissue, using the determined associations between the vascular network and the perfusion characteristics.

20 Claims, 8 Drawing Sheets

SYSTEM AND METHOD FOR VASCULAR TREE GENERATION USING PATIENT-SPECIFIC STRUCTURAL AND FUNCTIONAL DATA, AND JOINT PRIOR INFORMATION

RELATED APPLICATION(S)

This application claims priority to U.S. Provisional Application No. 62/145,714 filed Apr. 10, 2015, the entire disclosure of which is hereby incorporated herein by reference in its entirety.

FIELD OF THE DISCLOSURE

Various embodiments of the present disclosure relate generally to disease assessment, treatment planning, and related methods. More specifically, particular embodiments of the present disclosure relate to simulating vascular networks.

BACKGROUND

Coronary artery disease is a common ailment that affects millions of people. Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack. Significant strides have been made in the treatment of coronary artery disease including both medical therapy (e.g. statins) or surgical alternatives (e.g., percutaneous coronary intervention (PCI) and coronary artery bypass graft surgery (CABG)). Invasive assessments are commonly used to assess the type of treatment a patient may receive. However, indirect or noninvasive assessments for formulating a patient treatment are being explored and developed.

Heart disease is typically viewed as resulting from vessel disease, in particular, narrowing or blockage inside vessel lumens in a way that impacts blood flow. Currently, assessments to estimate perfusion may use perfusion scans, which may be costly and may expose the patient to unnecessary radiation. Thus, a desire exists to extend the functional analysis of fractional flow reserve (FFR) techniques to the perfused organ (i.e. the myocardium), and generate three dimensional (3D) models having a microvascular resolution, from the anatomical scans using available patient information to estimate a perfusion in a target tissue.

The foregoing general description and the following detailed description are exemplary and explanatory only and are not restrictive of the disclosure. For the purposes of the disclosure: "patient" may refer to any individual or person for whom diagnosis or treatment analysis is being performed, or any individual or person associated with the diagnosis or treatment analysis of one or more individuals; "electronic storage medium" may include, but is not limited to, a hard drive, network drive, cloud drive, mobile phone, tablet, or the like that may or may not be affixed to a display screen; "target tissue" may refer to the tissues and/or organ in which the blood supply may be estimated; and "imaging or scanning modalities" may refer to one or more techniques or processes used for visual representation, including but not limited to computerized tomography (CT), coronary computed tomography angiography (cCTA), positron emission tomography (PET), single photon emission computerized tomography (SPECT), magnetic resonance (MR) imaging, stress echo, correlation data and/or magnetic resonance (MR) imaging.

SUMMARY

According to certain aspects of the present disclosure, systems and methods are disclosed for generating a vascular tree model using joint prior information ("joint priors") and patient-specific structural and functional data.

One method includes: receiving a patient-specific vascular model of a patient's anatomy, including a vascular network comprising one or more arteries, arterioles, or capillaries; receiving a patient-specific target tissue model in which a blood supply may be estimated; receiving joint prior information associated with the vascular model and the target tissue model; receiving data related to one or more perfusion characteristics of the target tissue; determining, using a processor, one or more associations between the vascular network of the patient-specific vascular model and one or more perfusion characteristics of the target tissue using the joint prior information; and generating and outputting, using a processor, a vascular tree model that extends to perfusion regions in the target tissue, using the determined associations between the vascular network of the patient-specific vascular model and the perfusion characteristics of the target tissue.

In accordance with another embodiment, a system for generating a vascular tree model using joint priors and patient-specific structural and functional data under various physiological conditions comprises: a data storage device storing instructions for determining patient-specific perfusion characteristics; and a processor configured for: receiving a patient-specific vascular model of a patient's anatomy, including a vascular network comprising one or more arteries, arterioles, or capillaries; receiving a patient-specific target tissue model in which a blood supply may be estimated; receiving joint prior information associated with the vascular model and the target tissue model; receiving data related to one or more perfusion characteristics of the target tissue; determining, using a processor, one or more associations between the vascular network of the patient-specific vascular model and one or more perfusion characteristics of the target tissue using the joint prior information; and generating and outputting, using a processor, a vascular tree model that extends to perfusion regions in the target tissue, using the determined associations between the vascular network of the patient-specific vascular model and the perfusion characteristics of the target tissue.

In accordance with another embodiment, a non-transitory computer readable medium for use on a computer system containing computer-executable programming instructions for generating a vascular tree model using joint priors and patient-specific structural and functional data, the method comprising: receiving a patient-specific vascular model of a patient's anatomy, including a vascular network comprising one or more arteries, arterioles, or capillaries; receiving a patient-specific target tissue model in which a blood supply may be estimated; receiving joint prior information associated with the vascular model and the target tissue model; receiving data related to one or more perfusion characteristics of the target tissue; determining, using a processor, one or more associations between the vascular network of the patient-specific vascular model and one or more perfusion characteristics of the target tissue using the joint prior information; and generating and outputting, using a processor, a vascular tree model that extends to perfusion regions in the target tissue, using the determined associations between the vascular network of the patient-specific vascular model and the perfusion characteristics of the target tissue.

According to one aspect of the present disclosure, systems and methods are disclosed for using cardiac perfusion data as prior information for simulating microvascular networks to guide diagnosis or treatment of cardiovascular disease.

One method includes: receiving a patient-specific coronary model of a patient anatomy; receiving a patient-specific model of a target tissue in which a blood flow may be estimated; receiving patient-specific blood perfusion characteristics of the target tissue; determining, using a processor, an association between coronary arteries of the patient-specific coronary model and the perfusion characteristics of the target tissue using joint prior information from the patient-specific coronary model and the perfusion data; generating a complete vascular tree model extending to a microvascular scale by applying joint prior information from the coronary model and the blood perfusion characteristics of the target tissue; simulating a microvascular tree network extending from the coronary arteries to the associated perfusion regions of the target tissue; and outputting the complete 3D model of the coronary system with the extended microvascular tree network.

In accordance with another embodiment, a system for using cardiac perfusion data as prior information for simulating microvascular networks to guide diagnosis or treatment of cardiovascular disease comprises: a data storage device storing instructions for determining patient-specific perfusion characteristics; and a processor configured for: receiving a patient-specific coronary model of a patient anatomy; receiving a patient-specific model of a target tissue in which a blood flow may be estimated; receiving patient-specific blood perfusion characteristics of the target tissue; determining, using a processor, an association between coronary arteries of the patient-specific coronary model and the perfusion characteristics of the target tissue using joint prior information from the patient-specific coronary model and the perfusion data; generating a complete vascular tree model extending to a microvascular scale by applying joint prior information from the coronary model and the blood perfusion characteristics of the target tissue; simulating a microvascular tree network extending from the coronary arteries to the associated perfusion regions of the target tissue; and outputting the complete 3D model of the coronary system with the extended microvascular tree network.

In accordance with another embodiment, a non-transitory computer readable medium for use on a computer system containing computer-executable programming instructions for using cardiac perfusion data as prior information for simulating microvascular networks to guide diagnosis or treatment of cardiovascular disease, the method comprising: receiving a patient-specific coronary model of a patient anatomy; receiving a patient-specific model of a target tissue in which a blood flow may be estimated; receiving patient-specific blood perfusion characteristics of the target tissue; determining, using a processor, an association between coronary arteries of the patient-specific coronary model and the perfusion characteristics of the target tissue using joint prior information from the patient-specific coronary model and the perfusion data; generating a complete vascular tree model extending to a microvascular scale by applying joint prior information from the coronary model and the blood perfusion characteristics of the target tissue; simulating a microvascular tree network extending from the coronary arteries to the associated perfusion regions of the target tissue; and outputting the complete 3D model of the coronary system with the extended microvascular tree network.

According to one aspect of the present disclosure, systems and methods are disclosed for using intensity variation in anatomical data as prior information for simulating microvascular networks to guide diagnosis or treatment of cardiovascular disease.

One method includes: receiving a patient-specific coronary model of a patient anatomy; receiving a patient-specific model of a target tissue in which a blood flow may be estimated; measuring patient-specific intensity variations inside the target tissue; generating a trained model to predict a perfusion attenuation map from the intensity variations; determining, using a processor, an association between coronary arteries of the target tissue and the perfusion characteristics of the target tissue using joint prior information from the patient-specific coronary model and the perfusion data; generating a complete vascular tree model extending to a microvascular scale by applying the joint prior information from the coronary model and the blood perfusion characteristics of the target tissue; simulating a microvascular tree network extending from the coronary arteries to the associated perfusion regions of the target tissue; and outputting the complete 3D model of the coronary system with the extended microvascular tree network.

In accordance with another embodiment, a system for using intensity variation in anatomical data as prior information for simulating microvascular networks to guide diagnosis or treatment of cardiovascular disease comprises: a data storage device storing instructions for determining patient-specific perfusion characteristics; and a processor configured for: receiving a patient-specific coronary model of a patient anatomy; receiving a patient-specific model of a target tissue in which a blood flow may be estimated; measuring patient-specific intensity variations inside the target tissue; generating a trained model to predict a perfusion attenuation map from the intensity variations; determining, using a processor, an association between coronary arteries of the target tissue and the perfusion characteristics of the target tissue using joint prior information from the patient-specific coronary model and the perfusion data; generating a complete vascular tree model extending to a microvascular scale by applying the joint prior information from the coronary model and the blood perfusion characteristics of the target tissue; simulating a microvascular tree network extending from the coronary arteries to the associated perfusion regions of the target tissue; and outputting the complete 3D model of the coronary system with the extended microvascular tree network.

In accordance with another embodiment, a non-transitory computer readable medium for use on a computer system containing computer-executable programming instructions for using intensity variation in anatomical data as prior information for simulating microvascular networks to guide diagnosis or treatment of cardiovascular disease, the method comprising: receiving a patient-specific coronary model of a patient anatomy; receiving a patient-specific model of a target tissue in which a blood flow may be estimated; measuring patient-specific intensity variations inside the target tissue; generating a trained model to predict a perfusion attenuation map from the intensity variations; determining, using a processor, an association between coronary arteries of the target tissue and the perfusion characteristics of the target tissue using joint prior information from the patient-specific coronary model and the perfusion data;

generating a complete vascular tree model extending to a microvascular scale by applying the joint prior information from the coronary model and the blood perfusion characteristics of the target tissue; simulating a microvascular tree network extending from the coronary arteries to the associated perfusion regions of the target tissue; and outputting the complete 3D model of the coronary system with the extended microvascular tree network.

Additional objects and advantages of the disclosed embodiments will be set forth in part in the description that follows, and in part will be apparent from the description, or may be learned by practice of the disclosed embodiments. The objects and advantages on the disclosed embodiments will be realized and attained by means of the elements and combinations particularly pointed out in the appended claims.

It is to be understood that both the foregoing general description and the following detailed description are exemplary and explanatory only and are not restrictive of the detailed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Figure 1:
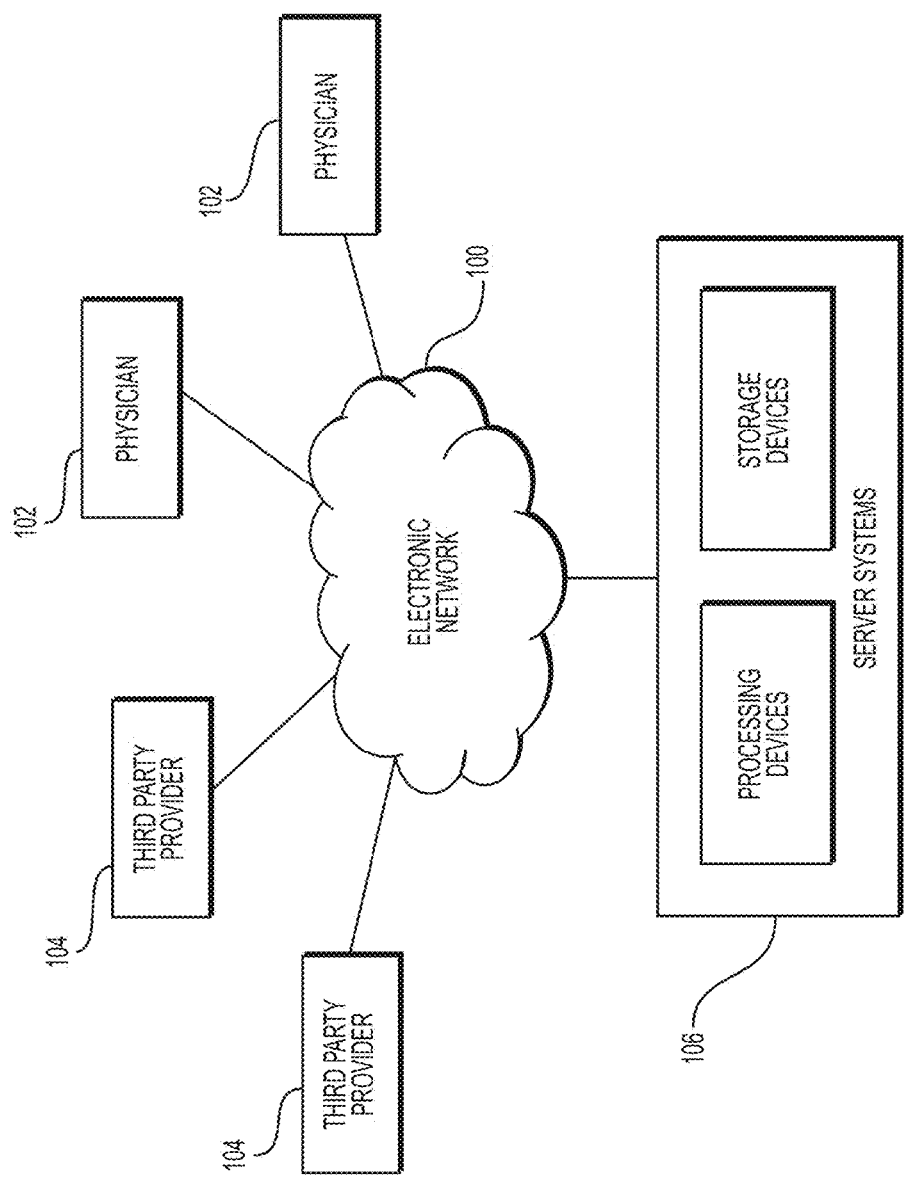
FIG. 1 is a block diagram of an exemplary system and network for predicting perfusion to guide diagnosis or treatment of cardiovascular disease, according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

Coronary artery disease is a common ailment, by which blood flow to the heart may be restricted. Restricted blood flow to tissues and/or other organs may be caused by diseased arteries leading thereto. While significant strides have been made in the treatment of coronary artery disease, the treatment is often misplaced or excessive. Due to the limited resolution of conventional anatomical scans, microvascular tree networks, including arterioles and capillaries, may not be adequately reconstructed from the captured images. Therefore, the health of the microvascular network in a target tissue and/or organ may not be adequately assessed. Thus, a need exists to simulate accurate microvascular networks within a target tissue from a vascular tree model in order to model the perfused tissue and simulate the blood flow therein. A generated microvascular tree model may be used to simulate tissue perfusion in a target organ without using invasive surgical treatments, or exposing a patient to additional perfusion scans which may be costly and/or expose the patient to unnecessary radiation.

Cardiovascular disease may be linked to vessel disease, meaning vessel narrowing or blockage. A cardiac perfusion scan may measure the amount of blood in the heart muscle at different physiological states, for example, while at rest, and during a non-rest state including, but not limited to, exercise or during physical activity. A perfusion scan is often performed to determine what may be causing chest pain and to determine if the tissue of the heart is supplied with an adequate flow of blood, or to determine how much heart muscle has been damaged from the heart attack.

During the scan, images of the heart are generated after a radioactive tracer is intravenously administered to the patient. The radioactive tracer travels through the blood and into the heart muscle. As the tracer moves through the heart muscle, tissues that have sufficient blood flow absorb the tracer. Tissue that does not absorb the tracer may not receive enough blood or may have been damaged by a heart attack. Two sets of images may be generated during a cardiac perfusion scan. One set of images may be generated while the patient is at rest ("at rest images"), while other sets of images may be generated while the patient is undergoing varied levels of stress-inducing physical activity ("non-rest images" or "stress images," respectively). The at rest images are then compared with the non-rest images or stress images and a level of perfusion in the target tissue may be determined.

Therefore, an understanding of perfusion in the target tissues, including the myocardium, may be clinically important. An understanding of perfusion may improve an evaluation of the severity of disease and of the appropriateness of treatment. In order to study perfusion in the target tissues, which may include microvascular networks, there is a desire for a system and method for simulating microvascular networks from a vascular tree model to simulate tissue perfusion under various physiological conditions.

The present disclosure describes a system and method for using available information to simulating a patient's microvascular network from a vascular tree model of a target tissue. The resulting vascular tree model may be used to simulate tissue perfusion under rest and stress conditions, and may enable the physician to forgo a perfusion scan in the diagnosis or treatment of cardiovascular disease. The present disclosure includes an exemplary approach incorporating prior knowledge from an upstream vascular model (e.g., spatial location of large vessel outlets, location and degree of stenosis, etc.) and/or prior knowledge from downstream tissues (eg., measured or estimated perfusion attenuation maps.) Such prior knowledge may be used to infer associations of arteries in an upstream model to perfused regions in downstream tissue region/model. For example, such associations may include determining segments of arteries that may correspond to regions of tissue and/or determining intraluminal or extraluminal geometries of artery segments that may contribute to perfusion levels within a region of tissue. The present disclosure further describes generating a more complete model of the patient-specific vascular tree (e.g., including patient-specific microvascular network(s)) from these associations. Use of prior knowledge may help produce microvascular tree model(s) that are anatomically and physiologically plausible. Additionally, the present disclosure describes simulating tissue perfusion for the patient using the model of the patient-specific vascular tree including microvascular network(s). Such simulations may involve simulating tissue perfusion under rest and stress conditions.

Figure 2:
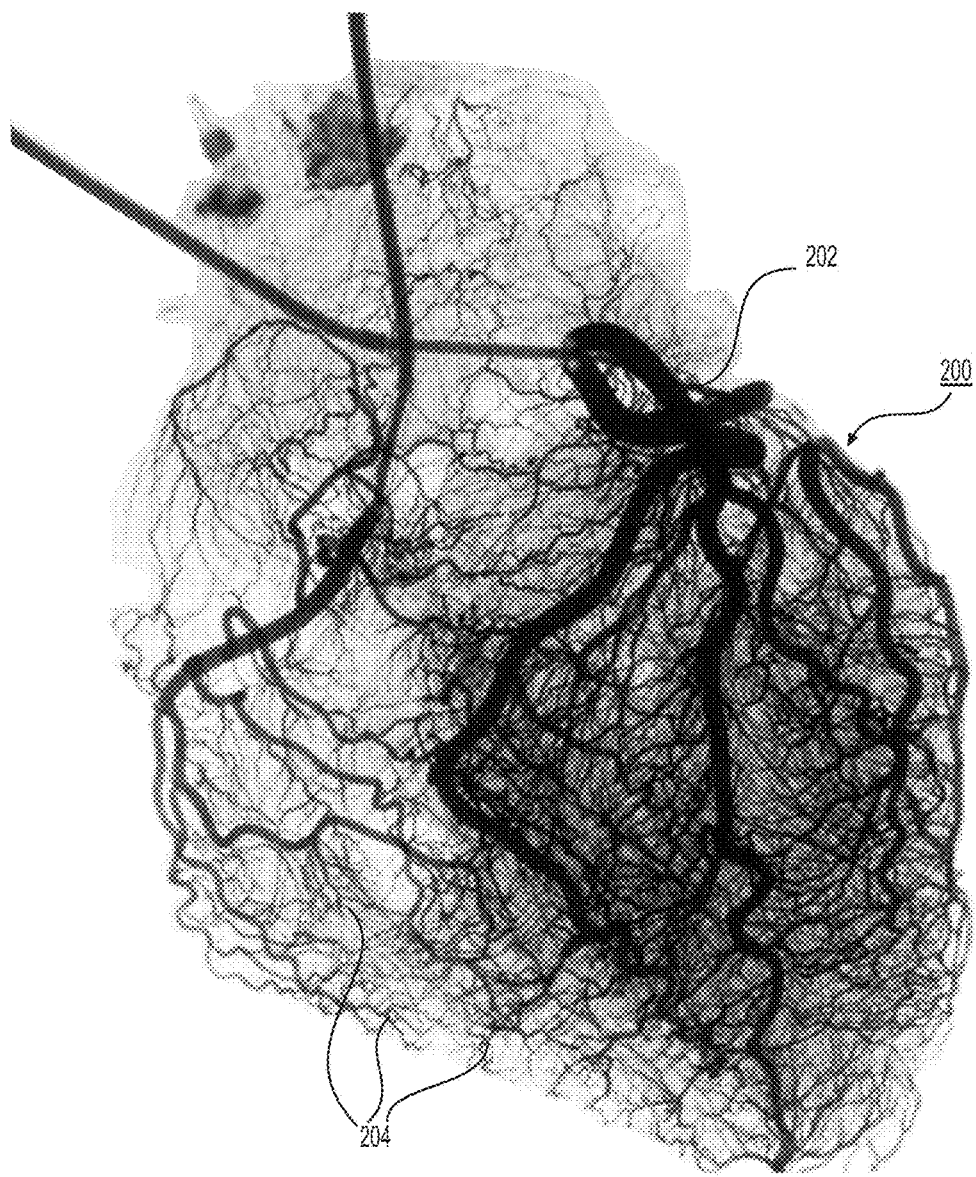
FIG. 2 is an illustration of an exemplary vascular tree network of an organ of a patient.
Figure 3:
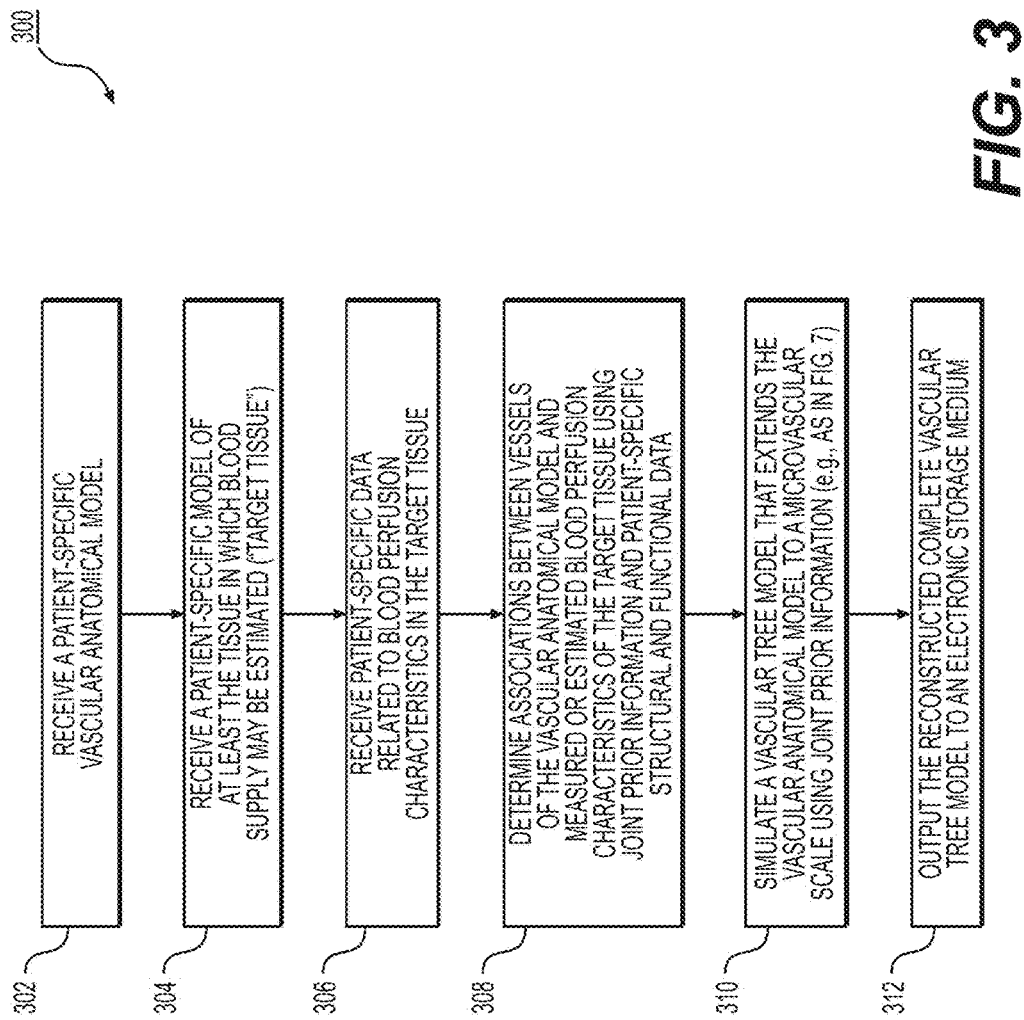
FIG. 3 is a block diagram of an exemplary method of generating a vascular and/or microvascular tree model.

The present disclosure may benefit patients and doctors by either estimating microvascular tree networks under conditions in which perfusion may be difficult to measure, and/or by using prior knowledge and/or measurements to more accurately assess the vasculature of an organ in different physiological conditions. As described above, FIG. 1 provides an overview of the system and network of the current disclosure, FIG. 2 depicts an exemplary vascular tree network, FIG. 3 illustrates a general embodiment of a method for generating a vascular and/or microvascular tree network, and FIGS. 4 and 5 each describe more specific embodiments of generating a vascular and/or microvascular tree network. Furthermore, FIGS. 3-5 each disclose an exemplary step of simulating a vascular tree model, for which an embodiment of the step may be described in detail in FIGS. 7A-7B. FIG. 5 describes an additional step that may be examined in detail in FIG. 6.

Referring now to the figures, FIG. 1 depicts a block diagram of an exemplary system 100 and network for estimating cardiac perfusion to guide diagnosis or treatment of cardiovascular disease, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices.

FIG. 2 depicts an exemplary vascular tree network of an organ of a patient (i.e., a myocardium). In one embodiment, the vascular model of an organ 200 may be imaged showing the arterial network 202 and may also have resolution depicting the microvascular networks 204.

Figure 4:
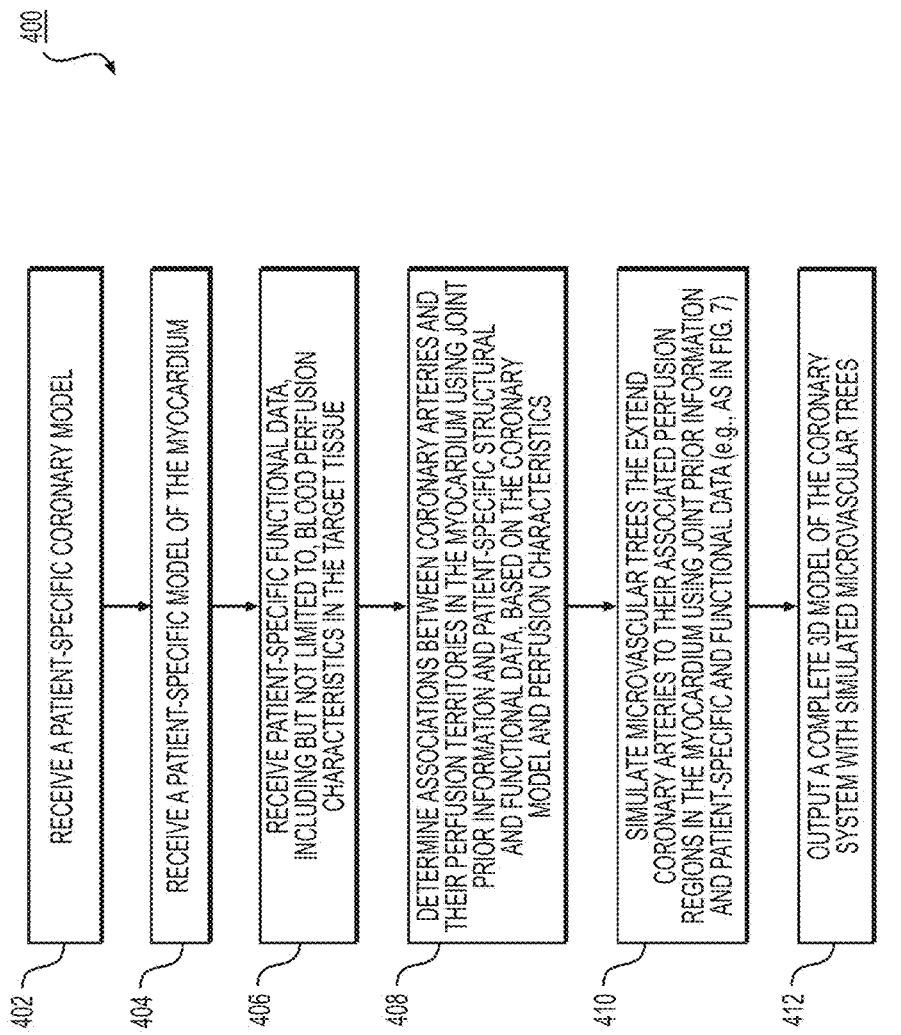
FIG. 4 is a block diagram of an exemplary method of generating a vascular and/or microvascular tree model using cardiac perfusion data.
Figure 5:
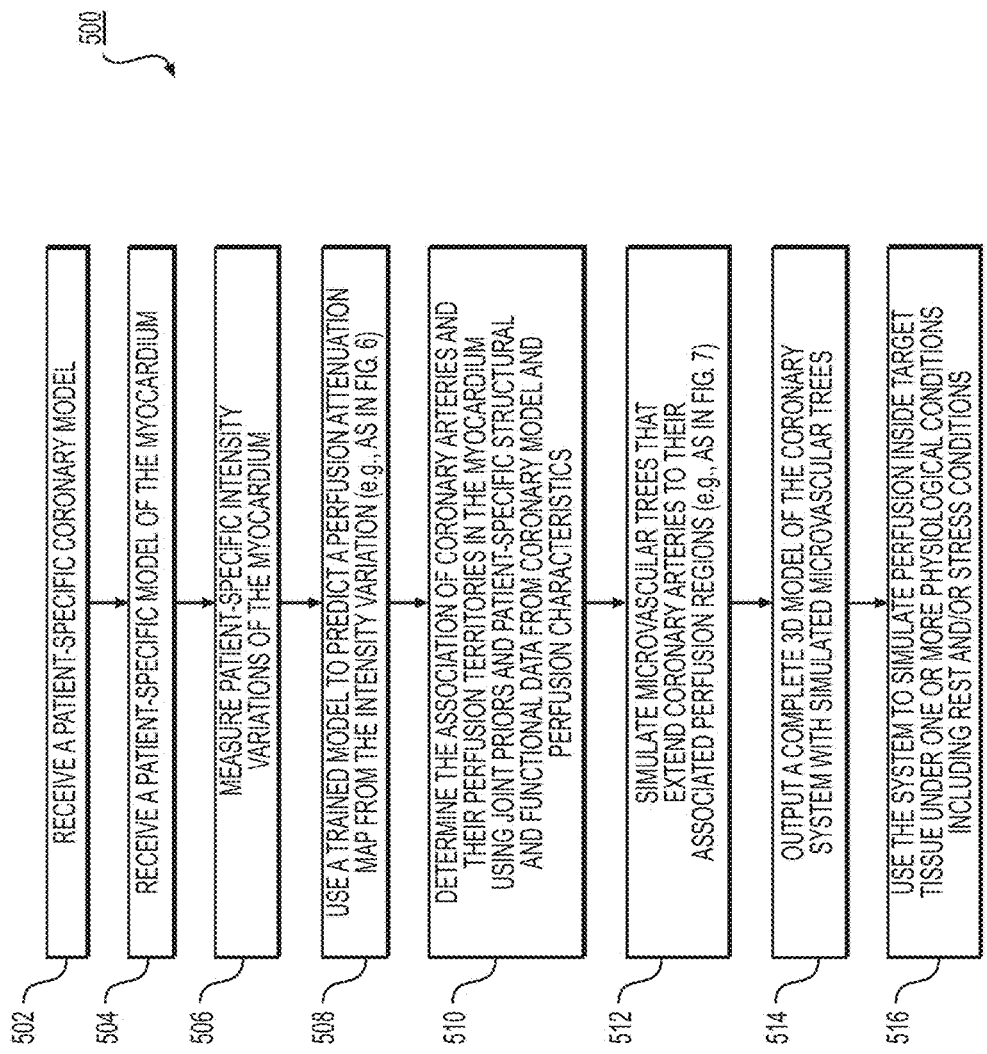
FIG. 5 is a block diagram of an exemplary method of generating a vascular and/or microvascular tree model using intensity variation data.

FIGS. 3 to 6 and 7A-7B illustrate general, exemplary, and specific embodiments of the disclosure and may provide further details on the steps involved in the methods disclosed. While FIG. 3 illustrates a general embodiment of a method for generating a vascular and/or microvascular tree network, FIG. 4 and FIG. 5 each describe more specific embodiments of the method of FIG. 3. For example, FIG. 4 illustrates a method for using cardiac perfusion data as prior information for microvasculature generation and simulation, and FIG. 5 illustrates a method for using intensity variations in anatomical data as prior information for microvasculature generation and simulation. Furthermore, the methods depicted in FIG. 3, FIG. 4, and FIG. 5 may include the steps of determining the association of vascular networks and their perfusion territories in a target tissue, and using a constrained constructive optimization approach for vascular and/or microvascular tree generation. An embodiment of the step of microvascular tree generation is described in more detail in FIGS. 7A-7B. The methods depicted in FIG. 5 may include the step of using intensity variations to predict perfusion attenuation, which is described in more detail in FIG. 6.

FIG. 3 depicts a general embodiment of an exemplary method 300 for estimating a complete vascular tree model of a target tissue to a microvascular scale.

In one embodiment, step 302 may include receiving a patient-specific vascular anatomical model in an electronic storage medium of the server system 106. Specifically, receiving the patient-specific vascular anatomic model may include either generating the patient-specific anatomical model at the server system 106, or receiving one over an electronic network (e.g., electronic network 101). The patient-specific vascular anatomical model may include, but is not limited to, the patient's cardiovascular system. In one embodiment, the vascular anatomical model may be derived from images of the person acquired via one or more available imaging or scanning modalities (e.g., coronary computed tomography angiography (cCTA) scans and/or magnetic resonance (MR) imaging). The vascular anatomical model may be obtained via segmentation of an imaging study, including, but not limited to, images obtained from one or more said available imaging or scanning modalities. The segmentation of the images may be performed by a processor.

In one embodiment, step 304 may include receiving a patient-specific model of the target tissue in an electronic storage medium. The tissue may be an organ including, but not limited to, the myocardium, the carotid artery, cerebral vasculature perfusing the brain, peripheral vasculature perfusing one or more muscles, renal vasculature supplying the kidney, and/or visceral vasculature supplying the bowels, liver, and/or spleen. In one embodiment, the patient-specific model of the target tissue may be obtained via segmentation of an imaging study, including, but not limited to, images obtained from one or more of said available imaging or scanning modalities. The segmentation of the images may be performed by a processor.

In one embodiment, step 306 may include receiving patient-specific data, which may be related to a blood perfusion attenuation characteristic in the target tissue. The patient-specific data may include, but is not limited to, data obtained from computerized tomography (CT) perfusion, positron emission tomography (PET), single photon emission computerized tomography (SPECT) perfusion, MR perfusion, stress echo, or correlation data. The patient-specific data may also relate to intensity variations per segment of the CT data in the target tissue, tissue wall thickness, wall motion, tissue viability, vessel size, vessel shape, vessel tortuosity, vessel length, vessel thickness, or a combination thereof.

In one embodiment, step 308 may include determining the association of the vascular and/or microvascular network of the patient-specific vascular anatomical model and the blood perfusion characteristics of the corresponding target tissues by using information, which may include, but is not limited to, the spatial location of the vessels and/or arteries, the topology of the arterial trees, the arterial geometry including size, length and tortuosity, the absence or presence of stenosis, the degree of stenosis, the type of plaques, and/or joint priors. The joint priors may include priors that may provide indication on the geometry and/or location of microvasculature, e.g., physiological priors (e.g., Murray's law, shape, appearance, etc.) and/or topological priors that are learned from existing data. In some embodiments, step 308 may include selecting the joint priors based on the received patient-specific information (e.g., from steps 302-306).

In one embodiment, step 310 may include generating a complete vascular tree model that extends the vascular anatomical model toward a more microvascular scale. The microvascular tree model may be constructed by applying joint prior information, patient-specific structural information, and/or patient-specific functional information from the vascular anatomical model and the measured and/or the estimated perfusion attenuation characteristics. In some embodiments, determining the vascular tree may include calculating an estimation of one or more of the anatomical characteristics of the vascular anatomical model. The anatomical characteristics may include, but are not limited to, vessel size, vessel shape, vessel tortuosity, vessel thickness, or a combination thereof. This calculation may be based on a measurement (e.g., by measuring the anatomical characteristics from imaging techniques) or via an estimation of the anatomical characteristics in a resting state (e.g., based on a three-dimensional (3D) simulation, a one-dimensional (1D) simulation, or a learned relationship). In some embodiments, the joint prior information may include, but is not limited to, the detected stenosis of the arteries in the target tissue. In one embodiment, step 310 may be performed by a processor.

One embodiment may include performing exemplary steps 308 and 310 as a single step, wherein a determined association of the vascular and/or microvascular network of the patient-specific vascular anatomical model and the blood perfusion characteristics of the corresponding target tissues may simultaneously produce, build, and/or optimize a model of a patient's microvascular tree network.

In one embodiment, step 312 may include outputting the reconstructed complete vascular tree model to an electronic storage medium. In one embodiment, the output vascular tree model may be displayed in greyscale or color in 2D or 3D. In the output model, one or more locations in the target tissue may be associated with a location on the vascular anatomical model.

FIG. 4 depicts an exemplary embodiment of method 400 for using cardiac perfusion data as prior information for the microvasculature simulation to guide diagnosis or treatment of cardiovascular disease. The method of FIG. 4 may be performed by server systems 106, based on information, images, and data received from physicians 102 and/or third party providers 104 over the electronic network 101.

In one embodiment, a cardiac perfusion scan may measure the blood flow transported to the various compartments of the myocardium, and compare the blood flow at a first physiological condition (i.e., a resting condition) and a second physiological condition (i.e., a non-resting and/or active state), in order to identify regions having blood perfusion deficits. In one embodiment, the measured perfusion data may provide a direct estimate of the perfusion distribution in the target tissue and/or organ. In one embodiment, an observed perfusion deficit region of a target tissue and/or organ may be supplied with blood by one or more diseased arteries.

In one embodiment, step 402 may include receiving a patient-specific coronary model in an electronic storage medium. In one embodiment, step 402 may include receiving a patient-specific model of any target tissue having a vascular and/or microvascular network, other than the coronary model. In one embodiment, the patient-specific coronary model may be derived from images of the person acquired via one or more available imaging or scanning modalities. The patient-specific coronary model may also be obtained via segmentation of an imaging study, including, but not limited to, images obtained from one or more said available imaging or scanning modalities, such as cCTA and/or MR. The segmentation of the images may be performed by a processor.

In one embodiment, step 404 may include receiving a patient-specific model of the myocardium in an electronic storage medium. In one embodiment, step 404 may include receiving a patient-specific model of a target tissue other than a myocardium. In one embodiment, the patient-specific model of the myocardium and/or target tissue may be obtained via segmentation of an imaging study, including, but not limited to, images obtained from one or more said available imaging or scanning modalities, such as cCTA and/or MR. The segmentation of the images may be performed by a processor.

In one embodiment, step 406 may include receiving patient-specific functional data, including, but not limited to, patient-specific perfusion data in an electronic storage medium. In one embodiment, the perfusion data may be registered and digitally overlaid on the myocardium model. Thus, the model of the myocardium and/or target tissue may show perfusion characteristics for each area of the vascular network. The patient-specific data may include, but is not limited to, data obtained from CT perfusion, positron emission tomography (PET) perfusion, single photon emission computerized tomography (SPECT) perfusion, MR perfusion, stress echo, or correlation data.

In one embodiment, step 408 may include determining the association of coronary arteries and their corresponding perfusion territories in the myocardium and/or target tissue by using joint prior information in conjunction with received patient-specific structural and functional data from the anatomical model and the perfusion map (e.g., from steps 402-406). In one embodiment, the joint prior information may include, but is not limited to, spatial location of the vessels and/or arteries, coronary geometry (including size, length and tortuosity, the absence or presence of stenosis), and/or physiological constraints (e.g., whether the image was taken during a stress, non-stress, or rest condition). In one embodiment, physiological constraints may include, for example, a constraint dictating that under-perfused regions of the myocardium and/or target tissue may be associated with diseased arteries.

Determining the association between the health of the arteries and the perfused regions of the myocardium and/or target tissue may be accomplished in several ways. In one embodiment, a location on the myocardium and/or target tissue may be associated with a coronary artery that is located closest thereto based on a Euclidean distance weighted by changes in the perfusion data such that variations in the perfusion data may be considered to increase the distance. In one embodiment, the perfusion data may be grouped via any standard technique, including, but not limited to, watershed techniques, k-nearest neighbors, k-means, mean shift, or super pixels etc., wherein each grouping is associated with the nearest coronary artery. In one embodiment, the myocardium and/or target tissue may be segmented into perfused regions using a shape model with a built-in association with the coronary arteries (or grouped arteries). The perfusion data may be used with the coronary artery model to drive model fitting.

In one embodiment, step 410 may include simulating the patient's microvascular trees that extend the coronary arteries to their associated perfusion regions in the myocardium and/or target tissues. In one embodiment, the simulation may take into account the received perfusion data. Microvascular trees may be grown via a constrained constructive optimization approach such that the tree growth may be biased to avoid crossing changes in the perfusion data. In other words, step 410 may include taking associations between coronary arteries and their perfusion territories from cardiac perfusion joint priors, and inferring a patient's microvascular tree from the patient's modeled coronary vasculature, modeled myocardium, and received/observed perfusion data based on those known associations. Analogously to steps 308 and 310 of FIG. 3, exemplary steps 408 and 410 may be performed as a single step.

In one embodiment, step 412 may include outputting the reconstructed vascular model to an electronic storage medium and/or to a display screen. In one embodiment, the output vascular model may be displayed in greyscale or color, and in 2D or 3D. In the output model, one or more locations in the target tissue may be associated with a location on the vascular anatomical model. In one embodiment, the system may be used to simulate perfusion inside the myocardium and/or target tissue under a variety of physiological conditions including, but not limited to, stress, non-stress, and/or rest conditions.

FIG. 5 depicts an exemplary embodiment of method 500 for using intensity variations in anatomical data as joint prior information and/or patient-specific structural and functional data for microvasculature generation and simulation to guide diagnosis or treatment of cardiovascular disease. A correlation may exist between the perfusion defects and the intensity variations per segment of CTA scans in the myocardium and/or target tissue. In some embodiments, intensity attenuation characteristics may be observed in under-perfused tissue regions. A model may be generated and trained to predict perfusion attenuation at various locations in the target tissue from a map generated from the intensity variation profiles in the myocardium and/or target tissue. The method of FIG. 5 may be performed by server systems 106, based on information, images, and data received from physicians 102 and/or third party providers 104 over electronic network 100.

In one embodiment, step 502 may include receiving a patient-specific coronary model of a target tissue or organ in an electronic storage medium. In one embodiment, step 502 may include receiving any patient-specific vascular anatomical model, other than the coronary model. In one embodiment, the patient-specific coronary model may be derived from images of the person acquired via one or more available imaging or scanning modalities, such as cCTA and/or MR. The patient-specific coronary model may also be obtained via segmentation of an imaging study, including, but not limited to, images obtained from one or more said available imaging or scanning modalities. The segmentation of the images may be performed by a processor.

In one embodiment, step 504 may include receiving a patient-specific model of a myocardium in an electronic storage medium. In one embodiment, step 504 may include receiving a patient-specific model of a target tissue other than a myocardium. In one embodiment, the patient-specific model of the myocardium and/or target tissue may be obtained via segmentation of an imaging study, including but not limited to, images obtained from one or more of said available imaging or scanning modalities. The segmentation of the images may be performed by a processor.

In one embodiment, step 506 may include measuring the patient-specific intensity variations per segment inside the myocardium and/or target tissue. In one embodiment, obtaining patient-specific intensity variations may involve the injection of a contrast agent (e.g., Gadolinium, Iodinated Contrast Medium, etc.) and measuring intensity curves over time. In one embodiment, obtaining patient-specific intensity variations may involve the use of one or more available imaging or scanning modalities.

In one embodiment, step 508 may include using a trained model to generate a perfusion attenuation map from an intensity variation map. The trained model may include determining, from a set of information, associations between perfusion and intensity variation of a CTA scan. For example, under-perfused tissue may correspond to areas of a myocardium with intensity under an expected intensity. Step 508 may include determining the trained model, and further determining, for the patient, a map of predicted perfusion attenuation, based on measured intensity variation (e.g., of step 506). Perfusion characteristics of various locations in the myocardium and/or target tissue may be estimated from the perfusion attenuation map (e.g., as described in more detail at FIG. 6).

In one embodiment, step 510 may include determining the association of the coronary arteries and their corresponding perfusion territories in the myocardium and/or target tissue by using joint prior information, patient-specific structural, and/or functional data from the coronary model and the perfusion map. In one embodiment, the joint prior information may include, but is not limited to, the spatial location of the vessels and/or arteries, the coronary geometry including size, length and tortuosity, the absence or presence of stenosis, and physiological constraints, such as whether the image was taken during a stress, non-stress, or rest condition. In one embodiment, the under-perfused regions of the target tissue may be associated with diseased arteries.

In one embodiment, step 512 may include simulating the microvascular trees that may extend coronary arteries to their associated perfusion regions in the myocardium and/or target tissues. In one embodiment, the simulation may take into account the received perfusion data. Microvascular trees may be grown via a constrained constructive optimization approach such that the tree growth may be biased to avoid crossing changes in the perfusion data. In other words, step 512 may include taking associations between coronary arteries and their perfusion territories from intensity attenuation/variation joint priors (and/or an intensity variation map), and inferring a patient's microvascular tree from the patient's modeled coronary vasculature, modeled myocardium, and received intensity variation of a patient's imaged myocardium based on those known associations. In one embodiment, an estimated perfusion attenuation map may be included as a spatial prior for simulating microvascular trees that may extend coronary arteries to their associated perfusion regions in the myocardium and/or target tissues. Analogously to steps 308 and 310 of FIG. 3, exemplary steps 510 and 512 may be performed as a single step.

In one embodiment, step 514 may include outputting the reconstructed complete vascular tree model to an electronic storage medium. In one embodiment, the output vascular tree model may be displayed in greyscale or color, and in 2D or 3D. In the output model, one or more locations in the target tissue may be associated with a location on the vascular anatomical model. In one embodiment, the system may be used to simulate perfusion inside the myocardium and/or target tissue under a variety of physiological conditions including, but not limited to, stress and/or rest conditions.

In one embodiment, step 516 may include calculating an estimation of the supplied blood to each area of the myocardium and/or target tissue under a first physiological state. One instance of a first physiological state may be a resting state. This calculation may be based on a measurement (e.g., by measuring by imaging) or via an estimation of supplied blood in a resting state (e.g., based on a 3D simulation, a 1D simulation, or a learned relationship).

In one embodiment, step 516 may include calculating an estimation of the supplied blood to each area of the myocardium and/or target tissue under a second physiological state. The second physiological state may be a physiological state other than the resting state, or an "active" or "stress" physiological state. One instance of such a physiological state may include hyperemia. Other non-resting physiological states may include various levels of exercise, post prandial, positional (e.g., supine-upright), gravitational (e.g., G-forces, zero gravity, etc.). Thus, step 516 may include determining an estimation of supplied blood at one or more vessel locations of the person's vascular model, while the person is in a hyperemic state. This determination may also be based on a measurement of blood flow (e.g., measurement using imaging) or via an estimation of blood flow in a resting state (e.g., based on a 3D simulation, a 1D simulation, or a learned relationship). In one embodiment, step 516 may further include determining, specifying, and/or selecting a physiological state as the "second physiological state" in comparing blood flow at a physiological state different from a patient resting state.

Figure 6:
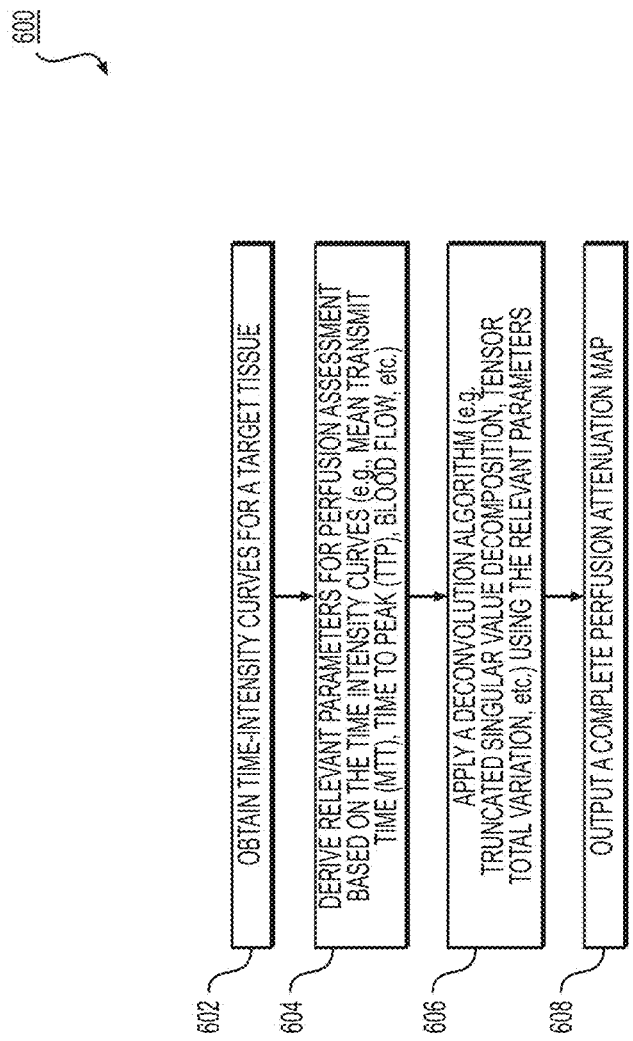
FIG. 6 is a block diagram of an exemplary method of using a trained model to predict perfusion characteristics from intensity variation data.

FIG. 6 depicts an exemplary embodiment of method 600, for predicting perfusion characteristics from intensity variation data. Method 600 may be included within method 500, which uses intensity variations in anatomical data as joint prior information and/or patient-specific structural and functional data for microvasculature generation and simulation, as step 508.

In one embodiment, step 602 may include obtaining time intensity curves of a target tissue. In one embodiment, obtaining time intensity curves may involve the injection of a contrasting agent (e.g., Gadolinium, Iodinated Contrast Medium, etc.). In one embodiment, obtaining time intensity curves may involve the use of one or more available imaging or scanning modalities. The time intensity curves may also be obtained via segmentation of the imaging study, including, but not limited to, images obtained from one or more of said available imaging or scanning modalities. The segmentation of the images may be performed by a processor. The target tissue may be an organ including, but not limited to, the myocardium, the carotid artery, cerebral vasculature perfusing the brain, peripheral vasculature perfusing one or more muscles, renal vasculature supplying the kidney, and/or visceral vasculature supplying the bowels, liver, and/or spleen.

In one embodiment, step 604 may include deriving relevant parameters for perfusion assessment based on the time intensity curves. In one embodiment, these relevant parameters for perfusion assessment may include, but are not limited to, the mean transit time (MTT) of a contrasting agent, time to peak (TTP), slope of the contrasting agent uptake, blood flow, blood volume, vascular permeability, and/or the area under the time intensity curve. The derivation of relevant parameters may be performed by a processor.

In one embodiment, step 606 may include applying a deconvolution-based algorithm using the relevant parameters from the time intensity curves to generate a perfusion attenuation map. In one embodiment, the deconvolution-based algorithm may be derived from the truncated singular value decomposition algorithm and/or the 4-D tensor total variation algorithm. In one embodiment, the deconvolution-based algorithm may be solved using a trained model. In one embodiment, step 606 may include using a non-deconvolution based algorithm (e.g., maximum slope method). The deconvolution based and/or non-deconvolution based algorithm may be performed by a processor.

In one embodiment, step 608 may include outputting a perfusion attenuation map to an electronic storage medium. In one embodiment, the outputted perfusion attenuation map may be displayed in greyscale or color, and in 2D or 3D.

Figure 7A:
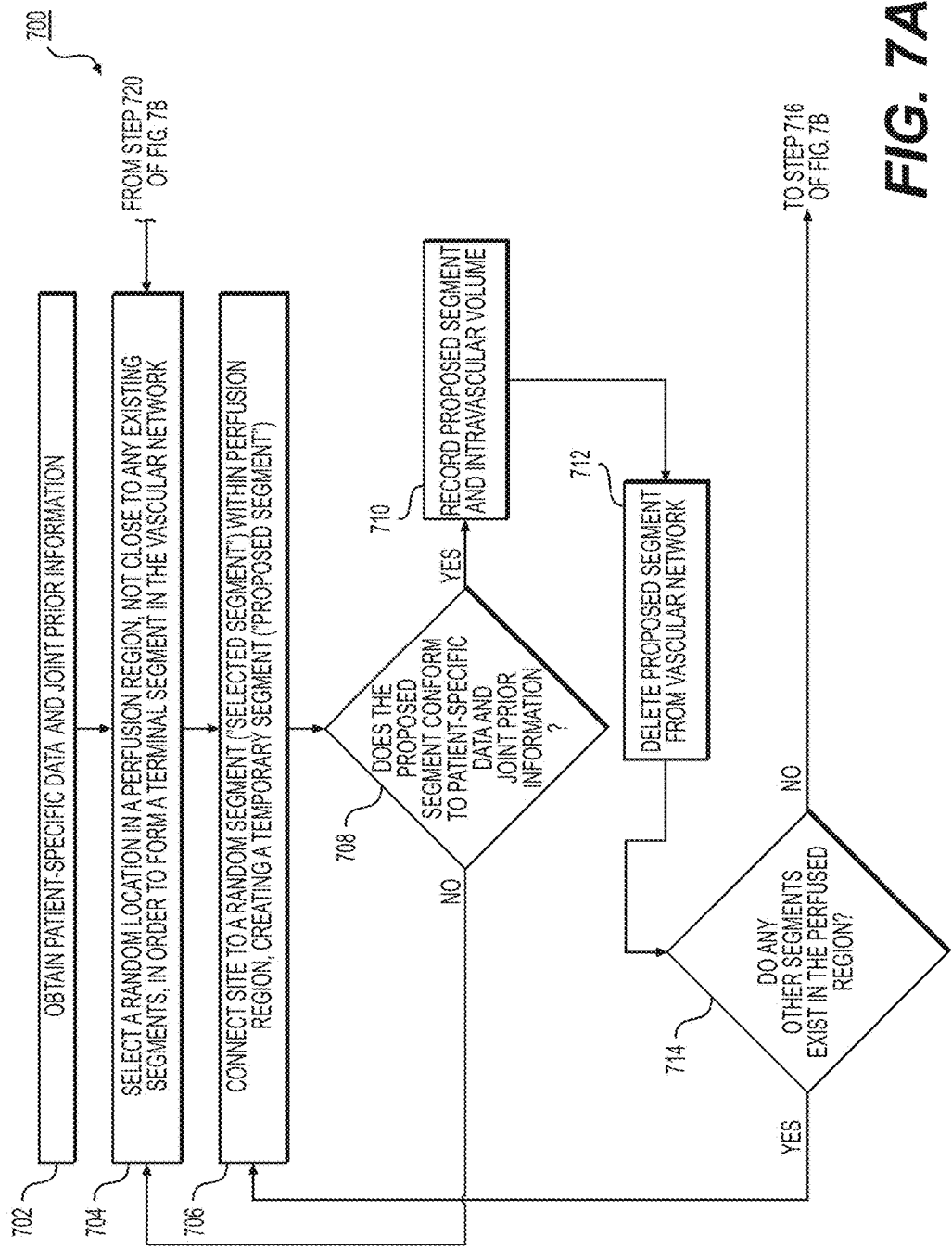
FIGS. 7A and 7B are block diagrams of an exemplary method for growing a vascular tree model using a constrained constructive optimization approach.
Figure 7B:
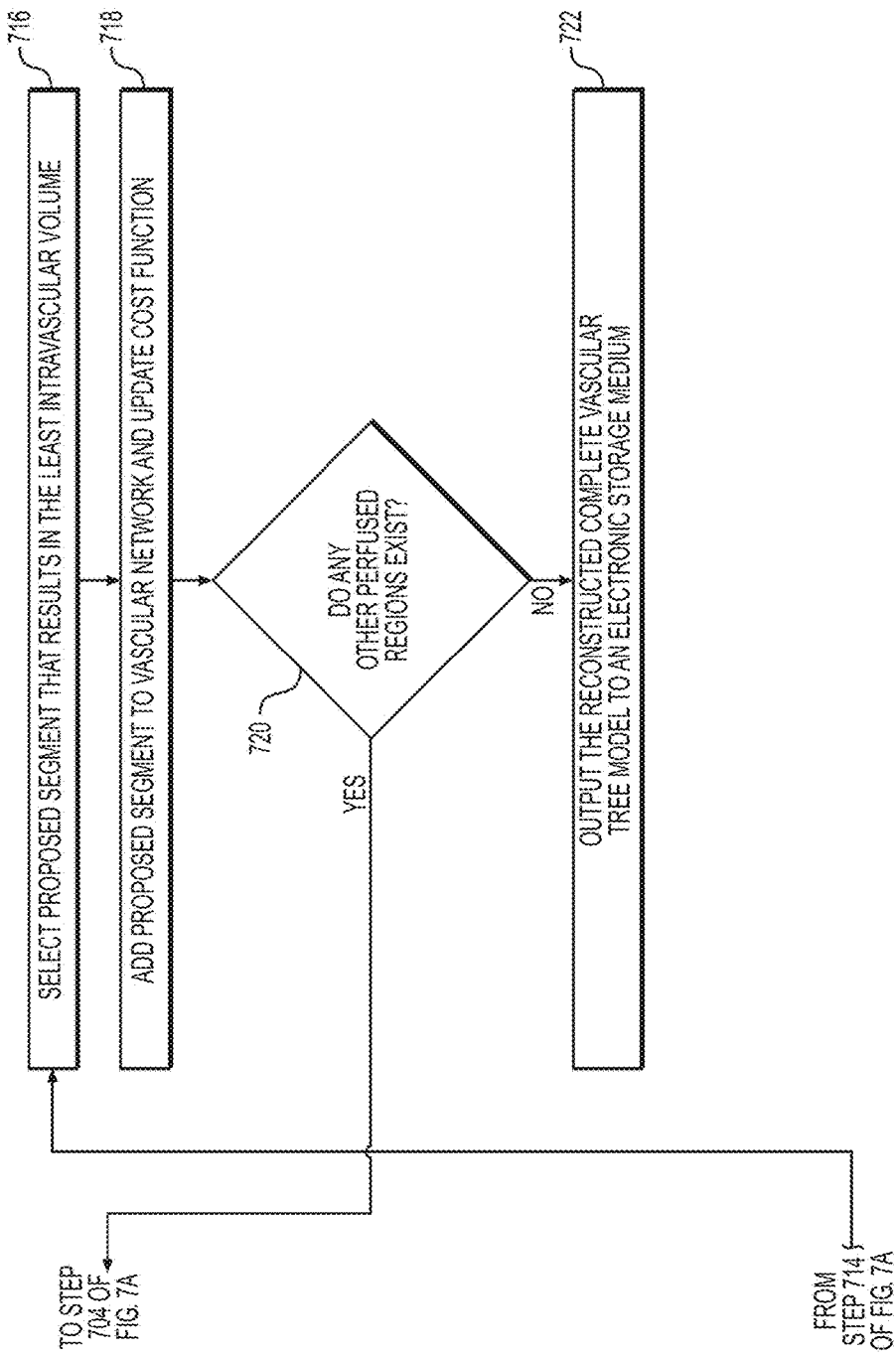

FIGS. 7A-7B depict exemplary embodiments of method 700 for growing a vascular tree model using constrained constructive optimization. In one embodiment, method 700 may be performed as part of method 300, which estimates a complete vascular tree model of a target tissue to a microvascular scale, as step 310. In another embodiment, method 700 may be performed as part of method 400, which uses cardiac perfusion data as prior information and/or patient-specific structural and functional data for microvasculature generation and simulation, as step 410. In one embodiment, method 700 may be performed as part of method 500, which uses intensity variations in anatomical data as prior information and/or patient-specific structural and functional data for microvasculature generation and simulation, as step 512.

In one embodiment, step 702 may include obtaining joint prior information and/or patient-specific structural and functional data. The patient-specific structural and functional data may include, but are not limited to, data obtained from CT perfusion, positron emission tomography (PET) perfusion, single photon emission computerized tomography (SPECT) perfusion, MR perfusion, stress echo, or correlation data. In one embodiment, the patient-specific structural and functional data may include intensity variation per segment of CT data in the target tissue, tissue wall thickness, wall motion, tissue viability, vessel size, vessel shape, vessel tortuosity, vessel length, vessel thickness, or a combination thereof. The joint prior information may include perfusion characteristics of a target tissue and associations between the perfused regions in a target tissue and the vascular and/or microvascular network. The target tissue may be an organ including, but not limited to, the myocardium, carotid, cerebral vasculature perfusing the brain, peripheral vasculature perfusing one or more muscles, renal vasculature supplying the kidney, and/or visceral vasculature supplying the bowels, liver, and/or spleen.

In one embodiment, step 704 may include selecting one or more random locations that is not close to any existing segments of the vascular and/or microvascular network, in a perfusion region of a target tissue, in order to form a new terminal segment that will add on to the vascular and/or microvascular network. In one embodiment, one or more locations may be grouped via any suitable technique, including, but not limited to, watershed techniques, k-nearest neighbors, k-means, mean shift, super pixels, etc., wherein each grouping is associated with the nearest coronary artery. In one embodiment, the selection may be performed by a randomization process. The selection may be performed by a processor.

In one embodiment, step 706 may include connecting the said one or more locations to a random segment ("selected segment") of the vascular and/or microvascular network in the perfusion region. This connection creates a bifurcation of the selected segment and temporarily creates a new segment ("proposed segment") connecting the said one or more locations to the selected segment in the vascular and/or microvascular network.

In one embodiment, step 708 may include determining, subsequent to step 706, whether the proposed segment conforms to the joint prior information and/or patient-specific structural and functional data. In one embodiment, step 708 may include determining whether the proposed segment intersects another segment. If, subsequent to step 708, the proposed segment does not conform to the patient-specific data or joint prior information, then in one embodiment, step 704 may be repeated. If subsequent to step 708, the proposed segment intersects with another segment of the vascular and/or microvascular network, then in one embodiment, step 704 may be repeated.

If, subsequent to step 708, the proposed segment does conform to the joint prior information and/or patient-specific structural and functional data, and the proposed segment does not intersect another segment, then, in one embodiment, step 710 may include recording the intravascular volume of the resulting microvascular and/or vascular network with the proposed segment added. In one embodiment, intravascular volume is defined as the volume of blood that the vascular and/or microvascular network could potentially hold with the proposed segment added in.

In one embodiment, step 712 may include deleting the proposed segment from the vascular and/or microvascular network once details regarding the proposed segment and intravascular volume have been recorded.

In one embodiment, step 714 may include determining whether there are other segments in the vicinity of the said one or more locations, within the perfused region, besides the previously selected segment. If, subsequent to step 716, there are other segments in the perfused region in the vicinity of the said one or more locations, then, in one embodiment, step 706 may be repeated with another selected segment and another proposed segment.

If, subsequent to step 714, there are no more segments in the vicinity of the said one or more locations, within the perfused region, besides previously selected segments, then, in one embodiment, step 716 may include selecting, from the recorded data, the proposed segment that results in the least intravascular volume.

In one embodiment, step 718 may include adding the proposed amendment with the least intravascular volume ("newly formed segment") into the vascular and/or microvascular network, and updating the patient-specific data and joint prior information.

In one embodiment, step 720 may include determining whether there are other perfusion regions in the target tissue, besides the perfusion region being supplied by the newly formed segment. If, subsequent to step 720, there are other perfusion regions in the target tissue, then, in one embodiment, step 704 may be repeated with another selected segment and another proposed segment within another perfusion region.

If, subsequent to step 720, there are no other perfusion regions, besides perfusion regions with newly formed segments, then, in one embodiment, step 722 may include outputting the reconstructed complete vascular tree model to an electronic storage medium. In one embodiment, the output vascular model may be displayed in greyscale or color in 2D or 3D. In the output model, one or more locations in the target tissue may be associated with a location on the vascular anatomical model. In one embodiment, the system may be used to simulate perfusion inside the target tissue under a variety of physiological conditions including, but not limited to, stress, non-stress, and/or rest conditions.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer implemented method for generating a vascular tree model, the method comprising:
    receiving a patient-specific vascular model of a patient's anatomy, the vascular model including a vascular network comprising one or more arteries, arterioles, or capillaries, the patient-specific vascular model being derived from one or more patient-specific images of the patient's anatomy;
    receiving a patient-specific target tissue model in which to estimate a blood supply, the patient-specific target tissue model being derived from the one or more patient-specific images of the patient's anatomy;
    receiving joint prior information associated with the vascular model and the target tissue model, the joint prior information including geometrical, physiological, and/or topological priors electronically learned from intensity variation data in the one or more patient-specific images of the patient's anatomy;
    receiving data related to one or more perfusion characteristics of the target tissue;
    determining, using a processor, one or more associations between the vascular network of the patient-specific vascular model and one or more perfusion characteristics of the target tissue using the joint prior information electronically learned from intensity variation data;
    generating, using a processor, a vascular tree model including a microvascular model that extends to perfusion regions in the target tissue, using the determined associations between the vascular network of the patient-specific vascular model and the perfusion characteristics of the target tissue;
    calculating an estimation of supplied blood to the target tissue according to the generated vascular tree model; and
    providing a diagnosis of cardiovascular disease according to the estimation of supplied blood to the target tissue.

2. The computer implemented method of claim 1, wherein data related to one or more perfusion characteristics include data obtained from CT perfusion scans, PET perfusion scans, SPECT perfusion scans, MR perfusion scans, data pertaining to stress echo information, correlation data, intensity variation data, vessel size, vessel shape, vessel tortuosity, vessel length, vessel thickness, or a combination thereof.

3. The computer implemented method of claim 1, wherein the anatomical characteristics of the vascular model include, one or more of:
    location and geometry of large vessel outlets;
    location and geometry of arteries, arterioles, and capillaries; and
    location and degree of stenosis.

4. The computer implemented method of claim 1, wherein, the patient-specific vascular model of a patient's anatomy, the target tissue model, or a combination thereof, is obtained via segmentation of the one or more images, including but not limited to CTA, PET, SPECT, or MR imaging techniques.

5. The computer implemented method of claim 1, wherein the patient-specific vascular model of a patient anatomy and the patient-specific target tissue model includes, one or more of:
    a coronary vascular model and a myocardium;
    a cerebral vascular model and a brain;
    a peripheral vascular model and a muscle;

a hepatic vascular model and a liver;
a renal vascular model and a kidney;
a visceral vascular model and a bowel; or
any target organ and vascular model with vessels supplying blood to said target organ.

6. The computer implemented method of claim 1, wherein the association between the vascular network of the patient-specific vascular model and the perfusion characteristics of the target tissue is determined by associating a location on the target tissue with the artery, arteriole, or capillary located closest with a Euclidean distance weighted by changes in the perfusion characteristics such that variations of the perfusion data may be considered in the distance computation.

7. The computer implemented method of claim 1, wherein the association between the vascular network of the patient-specific vascular model and the perfusion characteristics of the target tissue is determined by grouping the perfusion characteristics and associating each group with the nearest artery.

8. The computer implemented method of claim 7, wherein the grouping is performed via watershed techniques, k-nearest neighbors, k-means, mean shift, and/or superpixels.

9. The computer implemented method of claim 1, wherein the association between the vascular network of the patient-specific vascular model and the perfusion characteristics of the target tissue is determined by generating a vascular tree model, the association subsequently being used to generate another vascular tree model.

10. The computer implemented method of claim 1, wherein the association of the vascular network of the patient-specific vascular model and the perfusion characteristics of the target tissue is determined by segmenting the target tissue into perfused regions using a shape model with a built in association with the arteries.

11. The computer implemented method of claim 1, wherein the output vascular tree model associates each of a plurality of locations in the target tissue to an artery.

12. A system for generating a vascular tree model, the system comprising:
a data storage device storing instructions for generating a vascular tree model; and
a processor configured to execute the instructions to perform a method including the steps of:
receiving a patient-specific vascular model of a patient's anatomy, the vascular model including a vascular network comprising one or more arteries, arterioles, or capillaries, the patient-specific vascular model being derived from one or more patient-specific images of the patient's anatomy;
receiving a patient-specific target tissue model in which to estimate a blood supply, the patient-specific target tissue model being derived from the one or more patient-specific images of the patient's anatomy;
receiving joint prior information associated with the vascular model and the target tissue model, the joint prior information including geometrical, physiological, and/or topological priors electronically learned from intensity variation data in the one or more patient-specific images of the patient's anatomy;
receiving data related to one or more perfusion characteristics of the target tissue;
determining, using a processor, one or more associations between the vascular network of the patient-specific vascular model and one or more perfusion characteristics of the target tissue using the joint prior information electronically learned from intensity variation data;
generating, using a processor, a vascular tree model including a microvascular model that extends to perfusion regions in the target tissue, using the determined associations between the vascular network of the patient-specific vascular model and the perfusion characteristics of the target tissue;
calculating an estimation of supplied blood to the target tissue according to the generated vascular tree model; and
providing a diagnosis of cardiovascular disease according to the estimation of supplied blood to the target tissue.

13. The system of claim 12, wherein data related to one or more perfusion characteristics include the measured or estimated perfusion attenuation map or territory, data obtained from CT perfusion scans, PET perfusion scans, SPECT perfusion scans, MR perfusion scans, data pertaining to stress echo information, correlation data, intensity variation data, vessel size, vessel shape, vessel tortuosity, vessel length, vessel thickness, or a combination thereof.

14. The system of claim 12, wherein the anatomical characteristics of the vascular model include, one or more of:
location and geometry of large vessel outlets;
location and geometry of arteries, arterioles, and capillaries; and
location and degree of stenosis.

15. The system of claim 12, wherein the patient-specific vascular model of a patient anatomy and the patient-specific target tissue model includes, one or more of:
a coronary vascular model and a myocardium;
a cerebral vascular model and a brain;
a peripheral vascular model and a muscle;
a hepatic vascular model and a liver;
a renal vascular model and a kidney;
a visceral vascular model and a bowel; or
any target organ and vascular model with vessels supplying blood to said target organ.

16. The system of claim 12, wherein the association between the vascular network of the patient-specific vascular model and the perfusion characteristics of the target tissue is determined by associating a location on the target tissue with the artery, arteriole, or capillary located closest with a Euclidean distance weighted by changes in the perfusion characteristics such that variations of the perfusion data may be considered in the distance computation.

17. The system of claim 12, wherein the association between the vascular network of the patient-specific vascular model and the perfusion characteristics of the target tissue is determined by grouping the perfusion characteristics and associating each group with the nearest artery.

18. The system of claim 17, wherein the grouping is performed via watershed techniques, k-nearest neighbors, k-means, mean shift, and/or superpixels.

19. The system of claim 12, wherein the association between the vascular network of the patient-specific vascular model and the perfusion characteristics of the target tissue is determined by generating a vascular tree model, the association subsequently being used to generate another vascular tree model.

20. A non-transitory computer readable medium for use on a computer system containing computer-executable programming instructions for performing a method for generating a vascular tree model, the method comprising:
receiving a patient-specific vascular model of a patient's anatomy, the vascular model including a vascular network comprising one or more arteries, arterioles, or capillaries, the patient-specific vascular model being derived from one or more patient-specific images of the patient's anatomy;

receiving a patient-specific target tissue model in which to estimate a blood supply, the patient-specific target tissue model being derived from the one or more patient-specific images of the patient's anatomy;

receiving joint prior information associated with the vascular model and the target tissue model, the joint prior information including geometrical, physiological, and/or topological priors electronically learned from intensity variation data in the one or more patient-specific images of the patient's anatomy;

receiving data related to one or more perfusion characteristics of the target tissue;

determining, using a processor, one or more associations between the vascular network of the patient-specific vascular model and one or more perfusion characteristics of the target tissue using the joint prior information electronically learned from intensity variation data;

generating, using a processor, a vascular tree model including a microvascular model that extends to perfusion regions in the target tissue, using the determined associations between the vascular network of the patient-specific vascular model and the perfusion characteristics of the target tissue;

calculating an estimation of supplied blood to the target tissue according to the generated vascular tree model; and providing a diagnosis of cardiovascular disease according to the estimation of supplied blood to the target tissue.

* * * * *